United States Patent [19]

Schäfer et al.

[11] Patent Number: 4,617,186
[45] Date of Patent: Oct. 14, 1986

[54] SUSTAINED RELEASE DRUG DELIVERY SYSTEM UTILIZING BIOADHESIVE POLYMERS

[75] Inventors: Doris Schäfer; Rolf Schäfer, both of Arisdorf, Switzerland

[73] Assignee: Alcon Laboratories, Inc., Fort Worth, Tex.

[21] Appl. No.: 687,276

[22] Filed: Dec. 28, 1984

[51] Int. Cl.$^4$ ................ A61K 31/74; A61K 31/78
[52] U.S. Cl. ............................. 424/78; 424/81; 514/964
[58] Field of Search ...................... 424/78, 81

[56] References Cited

U.S. PATENT DOCUMENTS

| | | | |
|---|---|---|---|
| 2,703,777 | 3/1955 | Feinstein et al. | 167/59 |
| 2,798,053 | 7/1957 | Brown | 260/2.2 |
| 3,214,338 | 10/1965 | Ehrlich | 167/63 |
| 3,910,862 | 10/1982 | Barabas et al. | 260/79.3 |
| 3,911,105 | 10/1975 | Papantoniou et al. | 424/78 |
| 3,947,573 | 3/1976 | Rankin | 424/80 |
| 3,966,902 | 6/1976 | Chromecek | 424/59 |
| 3,980,769 | 9/1976 | Ghilardi et al. | 424/78 |
| 4,003,991 | 1/1977 | Krohn et al. | 424/81 |
| 4,271,143 | 6/1981 | Schoenwald et al. | 424/78 |
| 4,362,697 | 12/1982 | Tabb et al. | 422/56 |
| 4,407,792 | 10/1983 | Schoenwald et al. | 424/81 |
| 4,474,751 | 10/1984 | Haslam et al. | 424/78 |
| 4,478,822 | 10/1984 | Haslam et al. | 424/78 |

FOREIGN PATENT DOCUMENTS 2212392 9/1973 Fed. Rep. of Germany .
2173736 12/1973 France .

OTHER PUBLICATIONS

Schoenwald et al., "Influence of High-Viscosity Vehicles on Miotic Effect of Pilocarpine", *Journal of Pharmaceutical Sciences*, vol. 67, No. 9, (1978) 1280–1283.

Primary Examiner—Douglas W. Robinson
Attorney, Agent, or Firm—James A. Arno; Gregg C. Brown

[57] ABSTRACT

A sustained release drug delivery system suitable for ophthalmic use is described. The delivery system utilizes a cationic polymer (polyquat) to deliver a drug residue. The drug residue delivered may comprise an anionic drug or a drug-carrier complex.

12 Claims, No Drawings

SUSTAINED RELEASE DRUG DELIVERY SYSTEM UTILIZING BIOADHESIVE POLYMERS

BACKGROUND OF THE INVENTION

1. Field of the Invention

The present invention relates to sustained release drug delivery systems for use in the eye. More specifically, this invention relates to the use of high molecular weight cationic polymers having bioadhesive properties for the sustained release of ophthalmic preparations.

2. Description of Related Art

Simple aqueous drug dosage forms such as eye drops are widely used for the treatment of ophthalmic disorders. In many cases, these dosage forms are disadvantageous because the applied drug is rapidly removed from the eye through a mechanism of drug dilution and drug elimination caused by the continuous turnover of the tear fluid.

Sustained release drug systems which remain present on the eye for prolonged periods of time have been developed in the past based on the individual pharmacokinetics of the drugs to be released. These systems may include, for example, microscopical implants containing a semipermeable membrane which acts as a diffusion barrier and is responsible for sustained release of the principal active ingredient.

A significant drawback of the above described systems is the fact that these systems must be mechanically placed on the eye and subsequently, after completion of drug release, must be mechanically removed. The mechanical manipulations required with this type of system render the system unacceptable to many patients. There is therefore a need for a more convenient sustained release drug delivery system suitable for ophthalmic use.

Prior developments in connection with the use of high molecular weight polymers in ophthalmic dosage forms are described in U.S. Pat. Nos. 4,271,143 and 4,407,792. These patents relate to an aqueous dispersion of an ophthalmic drug and a high molecular weight polymer which forms a highly viscous gel and can be used to prolong the duration of activity of the ophthalmic drug when the gel is applied into the conjuctival sac of the eye. The high molecular weight polymers described in these patents include carboxyvinyl polymers (e.g., carboxypolymethylene) and ethylene maleic anhydride polymer.

SUMMARY OF THE INVENTION

A principal object of the present invention is the provision of a sustained release drug delivery system suitable for ophthalmic use.

Another object of this invention is the provision of an ophthalmic drug delivery system capable of providing sustained release of ophthalmic preparations in a convenient and reliable manner.

In order to satisfy the foregoing objects as well as other general objects of the present invention, there is provided a sustained release drug delivery system comprising a cationic polymer having bioadhesive properties and an anionic drug residue carried by said polymer.

DESCRIPTION OF THE PREFERRED EMBODIMENTS

This invention relates to the use of nontoxic, cationic polymers having bioadhesive properties, i.e., polymers capable of binding to eukaryotic cells or tissue, to form a sustained release drug delivery system. These polymers are capable of carrying, as counter ions, anionic drugs or drug release systems to form a sustained release system which can be conveniently applied to the eye in the form of more or less viscous eye drops, or in the form of a gel.

The cationic polymers utilized in the drug delivery system of the present invention comprise polymeric quaternary ammonium compounds (polyquats) of formula:

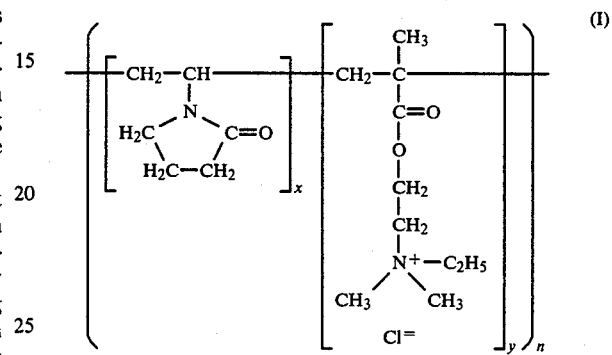

wherein: x, y and n are whole numbers such that the cationic polymers have a molecular weight ranging from about 50,000 to about 2,000,000, preferably about 100,000.

The above-described polymers are commercially available under the tradename "GAFQUAT" (manufactured by GAF). These polymers are described, for example, in U.S. Pat. No. 3,910,862; the contents of this patent relating to the composition, preparation and physical properties of cationic polymers of formula (I) are incorporated herein by reference. The commercially available polymers normally contain low molecular weight impurities which might be toxic. These impurities can be removed from the polymer by means of extensive dialysis conducted according to known techniques. For example, the counter ion ethylsulfate, which is toxic, is replaced by hydroxyl ions after dialysis with an aqueous solution of sodium hydroxide.

Using radiolabelled polymers of the above-described type, it has surprisingly been found that these compounds are bioadhesive, i.e., they strongly bind to monolayers of human epithelial cells and fibroblasts which were grown on collagenated supports in tissue cultures. Furthermore, the bioadhesive properties of these polymers have been demonstrated by the surprising observation that epithelial cells present in polymer-treated tissue cultures are removed from the collagen support as clusters of cells rather than as single cells as is the case in the absence of the polymers. The absence of toxic properties associated with the use of these polymers has been demonstrated by the fact that epithelial cells and fibroblasts are able to grow normally in the presence of the polymers.

In the absence of saline, the cationic polymer is able to tightly bind anionic drugs through salt formation. Examples of anionic drugs capable of binding with the cationic polymer include ketoprofen and suprofen. There are of course numerous other anionic drugs capable of binding with cationic polymers of formula (I) which may be utilized in the drug delivery system of the present invention. It should be noted that the cationic groups of the polymers can stoichiometrically bind anionic drugs; due to this fact, polymer drug complexes are often converted into insoluble formulations whereby the bioadhesiveness is completely lost. It has been demonstrated with radiolabelled polymers that the bioadhesiveness of the drug delivery system may be maintained if less than 50 percent of the cationic groups of the polymers carry anionic drug residues.

The cationic polymers utilized in the present invention also bind anionic carriers for sparingly soluble or insoluble drugs (e.g., carbonic anhydrous inhibitors, such as, acetazolamide and methazolamide); such carriers include liposomes prepared from phosphatidyl glycerol. Furthermore, these polymers bind microspheres prepared from albumin (i.e., albumin beads) which represent release systems for drugs having a high capacity for binding serum proteins; examples of these drugs include antibiotics such as tetracycline, penicillins and sulfonamides, and intraocular pressure lowering compounds such as betaxolol and pilocarpine.

It is important to note that the polymers utilized in the present invention are primarily ion exchange systems. Therefore, binding of a drug or a drug delivery system to the polymer occurs in aqueous solutions in the absence of saline. After application to the eye, the polymer-drug complex or the complex of polymer and drug delivery system binds initially to the tissue and is subsequently diluted with the tear fluid containing the ionic strength of a physiological salt solution. The ions of the tear fluid slowly penetrate the viscous polymer-drug complex or polymer-drug delivery system complex, whereby the active ingredient is slowly released from the polymer or the drug release system by means of an ion exchange mechanism.

The above-described complexes between polymer and drug, or polymer and drug delivery system such as charged liposomes or microspheres derived from albumin, possess bioadhesive and slow drug release properties, and as a result are very effective as sustained release systems for delivering ophthalmic drugs.

A preferred method of preparing the drug delivery system of the present invention may be described as follows. First, a cationic polymer of formula (I) is dissolved in aqueous media at concentrations of from about 0.1% to 5% (w/v), preferably 0.5 to 2%. Next, 0.5 charge equivalents of anionic drug (free acid), or 0.5 charge equivalents of drug-containing anionic lipids in the form of liposomes are added to one charge equivalent of the cationic polymer, thereby allowing binding of the drug or drug-containing delivery system to the polymer through salt formation. In the case of drug-containing albumin beads, 0.5 parts by weight are added to one part by weight of polymer. Nontoxic agents for use in sterilizing the system may also be used in combination with the sustained release formulations of the present invention, along with conventional formulatory ingredients such as preservatives, buffers, tonicity agents, and so on. The pH of the formulation is preferably from about 4.5 to 8.5.

The following examples further illustrate the present invention, but should not be interpreted as limiting the scope of the invention in any manner.

EXAMPLE 1

50 mg of a $^{14}C$-labelled (approximately 8,000 dpm) GAFQUAT-234 polymer (mol. wt. approximately 100,000) was prepared by transamination in the presence of 0.1 mg [$^{14}C$]-ethanolamine; unreacted ethanolamine was removed by dialysis. The labelled cationic polymer was then added to human embryonic fibroblasts at 70% confluence in 75 cm$^2$ collagen coated tissue culture flasks containing 25 mL of medium overlay. The medium overlay was removed 10 minutes after addition of the polymer and the radioactivity was determined in the medium overlay and in the cellular fraction.

It was determined that 46.2±2.5 mg of cationic polymer was absorbed by the fibroblasts. This result demonstrates the bioadhesiveness of the polymers utilized in the present invention.

EXAMPLE 2

50 mg of GAFQUAT-234 polymer (mol. wt. approximately 100,000) was added to an embryonic epithelial cell culture at 20% confluence. The tissue culture was incubated for one week. On the fifth day of incubation, the culture was as confluent as a control culture which did not receive polymer. From this data it was concluded that the polymers utilized in the present invention are not cytotoxic.

EXAMPLE 3

1 g of GAFQUAT-234 polymer (mol. wt. approximately 100,000) was dissolved in 10 mL of H$_2$O containing 0.1 g of suspended suprofen, a monobasic anionic drug. The heterogenous mixture was stirred at room temperature until homogeneous. In a different assay, 1 g of the same polymer was dissolved in 10 mL of H$_2$O containing 0.5 g of phosphatidylglycerol liposomes and 0.1 g of suprofen sodium salt. As controls, assays of 0.1 g suprofen sodium salt dissolved in 10 mL of H$_2$O and in 10 mL of H$_2$O containing 0.5 g of phosphatidylglycerol liposomes were prepared. Each formulation was dialyzed against 100 mL saline.

The amount of drug released was determined spectrophotometrically in the outer dialysate as a function of time of dialysis. Based on kinetical measurements, it was determined that 50% of the suprofen sodium salt was released to the outer dialysate after 16 minutes in the absence of liposomes and after 28 minutes in the presence of liposomes (controls), while 50% of suprofen was released from the polymer-drug complex to the outer dialysate after 130 minutes and 50% of suprofen was released from the complex of polymer and liposomes to the outer dialysate after 165 minutes. These results demonstrate the sustained release properties of the present drug delivery systems.

The invention has been described herein with reference to certain preferred embodiments. However, as obvious variations thereon will become apparent to these skilled in the art, the invention is not to be considered as limited thereto.

We claim:

1. A sustained release drug delivery system suitable for ophthalmic use, comprising a cationic polymer of formula:

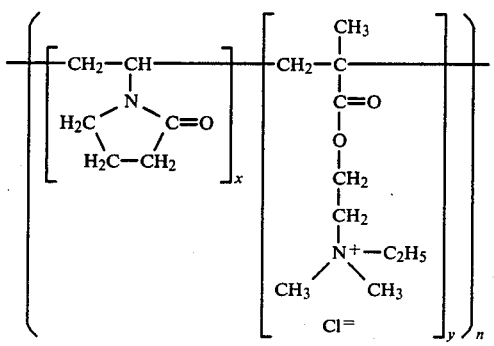

wherein: x, y and n are whole numbers such that the cationic polymer has a molecular weight of from about 50,000 to about 2,000,000; and a therapeutically effective amount of an anionic drug residue carried by said polymer.

2. The drug delivery system according to claim 1, wherein the drug residue is selected from the group consisting of anionic drugs and insoluble drugs carried by an anionic carrier.

3. The drug delivery system according to claim 2, wherein the drug residue comprises an anionic drug.

4. The drug delivery system according to claim 3, wherein the anionic drug comprises suprofen.

5. The drug delivery system according to claim 2, wherein the drug residue comprises an insoluble drug carried by an anionic carrier.

6. The drug delivery system according to claim 5, wherein the anionic carrier comprises liposomes prepared from phosphatidyl glycerol.

7. The drug delivery system according to claim 1, wherein the drug residue comprises a drug carried by microspheres prepared from albumin.

8. The drug delivery system according to claim 1, wherein the molecular weight of the polymer is about 100,000.

9. The drug delivery system according to claim 1, wherein less than 50 percent of the cationic groups of the polymer carry an anionic drug residue.

10. A sustained release ophthalmic dosage-form, comprising a cationic polymer of formula:

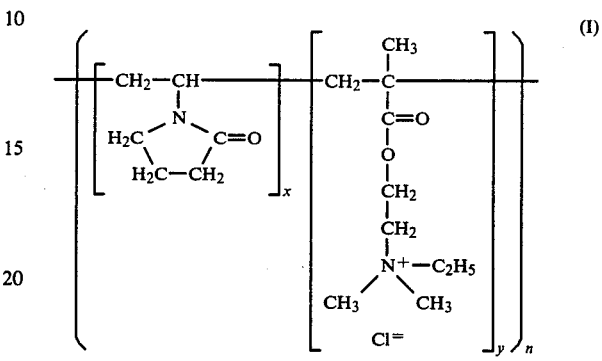

wherein: x, y and n are whole numbers such that the cationic polymer has a molecular weight of from about 50,000 to about 2,000,000; and a therapeutically effective amount of an anionic drug residue carried by said polymer, wherein less than 50 percent of the cationic groups of the cationic polymer carry said anionic drug residue.

11. The ophthalmic dosage form according to claim 10, wherein the anionic drug residue comprises suprofen.

12. The ophthalmic dosage form according to claim 11, wherein the molecular weight of the polymer is about 100,000.

* * * * *